United States Patent [19]

Kadri

[11] Patent Number: 5,706,829

[45] Date of Patent: Jan. 13, 1998

[54] METHOD FOR TREATING NEUROCARDIOGENIC SYNCOPE

[75] Inventor: Nazih Najih Kadri, Omaha, Nebr.

[73] Assignee: Creighton University, Omaha, Nebr.

[21] Appl. No.: 660,798

[22] Filed: Jun. 6, 1996

[51] Int. Cl.$^6$ .................................................. A61B 19/00
[52] U.S. Cl. ........................ 128/898; 514/220; 514/338
[58] Field of Search ................................ 128/898, 897; 514/220, 338; 540/507; 548/498; 604/890.1, 891.1

[56] References Cited

U.S. PATENT DOCUMENTS

| | | |
|---|---|---|
| 3,116,203 | 12/1963 | Kariss et al. . |
| 3,121,114 | 2/1964 | Keller et al. . |
| 3,123,529 | 3/1964 | Kariss et al. . |
| 3,203,990 | 8/1965 | Keller et al. . |
| 3,335,181 | 8/1967 | Focella et al. . |
| 4,472,397 | 9/1984 | Lahti et al. . |
| 4,772,599 | 9/1988 | Watjen . |
| 5,284,491 | 2/1994 | Sutton et al. . |
| 5,302,715 | 4/1994 | Buechler et al. . |
| 5,317,018 | 5/1994 | Walser et al. . |
| 5,409,946 | 4/1995 | Garvey et al. ............ 514/372 |
| 5,501,701 | 3/1996 | Markowitz et al. . |

OTHER PUBLICATIONS

Goodman and Gilman, "The Pharmacological Basis of Therapeutics" fourth edition. pp. 177–181, 1970.
Sugimoto, et al. "The effects of diazepam on rat isolated heart muscle." Clinical and Experimental Pharmacology and Physiology. 5:655–663, 1978.
Defeudis, F.V. "GABA and 'neuro–cardiovascular' mechanisms." Neurochemistry International. 3(2): 113–121, 1981.
Petersdorf, et al, eds. "Harrison's Principles of Internal Medicine." 1983. pp: 76–80, 1298, 2025–2027, 2106, 1983.
Raza, et al. "Comparison of the hemodynamic effects of midazolam and diazepam in patients with coronary occlusion." International Journal of Clinical Pharmacology, Therapy and Toxicology, 27(Jan. 1989): 1–6, 1989.
Osman, et al. "Dose–dependent effects of intravenous alprazolam on neuroendocrine, biochemical, cardiovascular, and behavioral parameters in humans." Psychopharmacology. 111:295–300, 1993.
Abi–Samra et al., Pacing Clin Electrophysiol 11(8): 1202–1214 (1988).
Fitzpatrick et al., Pacing Clin Electrophysiol 13(5): 619–624 (1991).
Kapoor, JAMA 268(18): 2553–2560 (1992).
Kenny et al., Lancet 1(8494): 1352–1355 (1986).
Kosinski et al., Pacing Clin Electrophysiol 18(4 Pt 1): 716–724 (1995).
Lipton and Forstater, J Emerg Med 11(6): 723–727 (1993).
Milstein et al., Am J Cardiol 65(20): 1339–1344 (1990).
Natale et al., Pacing Clin Electrophysiol 18(4 Pt 1): 655–662 (1995).
Sra et al., Cardiol Clin 11(1): 183–191 (1993).
Sra et al., N Engl J Med 328(15): 1085–1090 (1993).
Sternbach et al., J Med Chem 6:261–265 (1963).
Sato and Malow, in Antiepileptic Drugs, 4th Edition, edited by R.H. Levy et al., Raven Press, Ltd., New York, pp. 725–734 (1995).
The Merck Index, 10th Edition, edited by W. Windholz et al., Merck & Co., Inc., Rahway, New Jersey, p. 2351 #2352 (1983).
The Physicians' Desk Reference, 39th Edition, publisher E.R. Barnhart, Medical Economics Company Inc., Oradell, New Jersey pp. 429, 1680–1681 (1985).
Kadri et al., Abstract from the 17th Annual Meeting of the North American Society of Pacing and Electrophysiology, published Apr. 1996.

Primary Examiner—Vincent Millin
Assistant Examiner—Kelly R. O'Hara
Attorney, Agent, or Firm—Jaeckle Fleischmann & Mugel, LLP

[57] ABSTRACT

The present invention relates to methods for treating neurocardiogenic syncope. The method involves administering to a patient an effective amount of a compound having the formula:

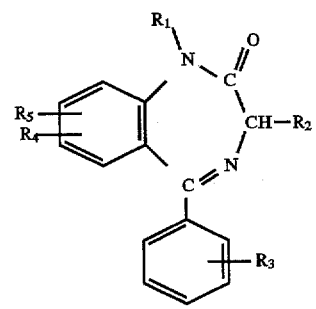

wherein $R_1$, $R_2$ and $R_5$ are each selected from the group consisting of hydrogen and lower alkyl; and $R_3$ and $R_4$ are each selected from the group consisting of hydrogen, halogen, lower alkyl, nitro, amino, trifluoromethyl, and lower acylamino; at least one of $R_3$ and $R_4$ being a nitrogen containing group, or a pharmaceutically acceptable salt thereof.

21 Claims, No Drawings

METHOD FOR TREATING NEUROCARDIOGENIC SYNCOPE

FIELD OF THE INVENTION

The present invention relates to methods for treating neurocardiogenic syncope, and more particularly to the use of benzodiazepines such as clonazepam to treat such a disorder.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Neurocardiogenic syncope is a collective term used to describe the clinical syndromes of syncope that result from inappropriate, and often excessive, autonomic reflex activity, and manifest as abnormalities in the control of vascular tone and heart rate. These include carotid sinus syndrome, vasovagal syncope, and the syndromes of cough, deglutition, and micturition syncope (Sutton and Petersen 1995). "Syncope" refers to the sudden transient loss of consciousness (fainting) associated with the inability to maintain postural tone. "Pre-syncope" refers to premonitory signs and symptoms of imminent syncope, including pallor, sighing, hyperventilation, nausea, diaphoresis, blurred vision, impaired hearing, feeling of unawareness, and palpitations. Syncope can also occur without such premonitory signs and symptoms.

Neurocardiogenic syncope can be induced by a variety of conditions, including but not limited to, auditory and visual stimuli, hypovolemia, severe anxiety, situations which produce sympatho-adrenal discharge with resultant increase in myocardial contractility, and on occasion it may occur without apparent precipitating factors. Vasovagal syncope is a condition marked by a sudden drop in heart rate and/or blood pressure, resulting in fainting. It is not only unpleasant for a patient, but potentially dangerous, as fainting may lead to injuries from falls. Vasovagal syncope is generally precipitated by fear, emotional stress, or pain. For example, patients with blood-injury phobia can suffer vasovagal syncope in response to common venipuncture (Lipton and Forstarer 1993).

Lipsitz et al. reported that among elderly patients (75 years or older) there is a 6% annual incidence of unexplained syncope with recurrence rate of 30%. Causes of syncope include situational syncope (1–8%), orthostatic hypotension (4–12%), drug-induced syncope (2–9%), organic cardiac disease (3–11%), arrhythmias 5–30%), vasovagal (1–29%), and unknown (38–47%).

Classically, neurocardiogenic syncope is diagnosed by exclusion of other diagnoses, as well as by reproducing the clinical signs and symptoms by utilization of the head up tilt test. During this test while the patient is supported on a bed, the bed is tilted to 35° for three minutes and then up to 70° for 45 minutes or until pre-syncope occurs. A positive test for neurocardiogenic syncope is one that causes symptomatic hypotension, bradycardia, or both. A normal physiologic response to head up tilt test (negative test) consists of an increase in heart rate, increase in diastolic pressure, and slight decrease in systolic pressure with little or no change in mean arterial pressure. The head up tilt test has gained broad acceptance as a reliable diagnostic method for the assessment of patients with recurrent unexplained syncope (Fitzpatrick et al. 1989; Fitzpatrick et al. 1991a; Fouad et al. 1993; Grubb et al. 1992a; Grubb et al. 1992b; Raviele et al. 1990; Grubb et al. 1993; Grubb et al. 1991; Chen et al.) Other diagnostic methods include prolonged electrocardiographic monitoring and electrophysiologic studies.

Once the diagnosis of syncope is reached, there is no consensus on the most appropriate treatment. In this respect, efficacy of existing drug therapy in preventing recurrence of symptoms in patients is not entirely clear, and controversies exist regarding the need to confirm the effects of pharmacological interventions. Natale et al. (1995) assessed different therapeutic approaches to patients diagnosed by the head up tilt test. Of 303 patients, 44 received empiric therapy, 210 were treated with medications proven effective during repeated head up tilt testing, and 49 refused or discontinued medical therapy. Among the patients treated according to head up tilt guided therapy, 130 were on beta blockers, 35 on theophylline, 10 on ephedrine, 31 on disopyramide, and 4 on miscellaneous regimens. Empiric treatment consisted of beta blockers in 37 of 44 patients and other drugs in the remaining patients. During the follow-up, recurrence of symptoms was experienced in 12 (6%) of the 210 patients receiving the head up tilt guided therapy, 16 (36%) of 44 in the empiric therapy group, and 33 (67%) of 49 in the no therapy group. Recurrence of symptoms in patients on empiric or no therapy was significantly more frequent as compared to the head up tilt guided therapy group.

Sra et al. (1993b) compared the efficacy of permanent cardiac pacing in patients with neurocardiogenic syncope associated with bradycardia or asystole with that of oral drug therapy in the prevention of hypotension and syncope during head up tilt testing. Among 70 patients with a history of syncope in whom hypotension and syncope could be provoked during head up tilt testing, 22 had bradycardia (a heart rate <60 beats per minute, with a decline in the rate by at least 20 beats per minute) or asystole along with hypotension during testing. Head up tilt testing was repeated during atrioventricular sequential pacing (in 20 patients with sinus rhythm) or ventricular pacing in 2 patients with atrial fibrillation). Regardless of the results obtained during artificial pacing, all the patients subsequently had upright tilt testing repeated during therapy with oral metoprolol, theophylline, or disopyramide. During the initial tilt test, 6 patients had asystole and 16 had bradycardia along with hypotension. Despite artificial pacing, the mean arterial pressure during head up tilt testing still fell significantly. Five (5) patients had syncope, and 15 had presyncope. By contrast, 19 patients who later received only medical therapy (metoprolol in 10, theophylline in 3, and disopyramide in 6), 2 patients who received both metoprolol and atrioventricular sequential pacing, and 1 patient who received only atrioventricular sequential pacing, had negative head up tilt tests. After a median follow-up of 16 months, 18 of the 19 patients who were treated with drugs alone (94%) remained free of recurrent syncope or pre-syncope, whereas the patient treated only with permanent dual-chamber pacemaker had recurrent syncope. Thus, drug therapy was more effective than artificial pacing.

Therapies for neurocardiogenic syncope have included volume expansion, beta blockers, transdermal scopolamine (Abi-Samra et al. 1988), Norpace or disopyramide (Milstein et al. 1990), Florinef (mineralocorticoids/glucocorticoids), and cardiac pacing (Kenny et al. 1986; Fitzpatrick et al. 1991b; Sra et al. 1993b). Cardiac pacing as a treatment of vasovagal syncope is disclosed in U.S. Pat. No. 5,501,701 of Markowitz and Hess and in U.S. Pat. No. 5,284,491 of Sutton et al.

For general discussions of diagnosis, mechanisms, and/or treatment of neurocardiogenic syncope, see Sra et al. 1993a; Kosinski et al. 1995;Kapoor 1992;and Natale et al. 1995.

Patients with neurocardiogenic syncope may, on occasions, be prevented from driving or from being in any place by themselves where if they faint they could endanger their life or the lives of others. With the control of neurocardiogenic syncope, the patients may lead a normal life. A need remains, therefore, for effective methods of treating neurocardiogenic syncope. The present invention is directed to meeting this need.

SUMMARY OF THE INVENTION

The present invention relates to methods for treating neurocardiogenic syncope.

In one aspect of the present invention, the method includes administering to the patient an effective amount of a benzodiazepine, such as the benzodiazepine having the formula:

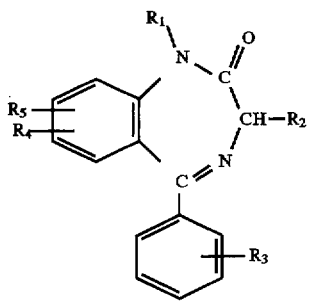

wherein $R_1$, $R_2$ and $R_5$ are each selected from the group consisting of hydrogen and lower alkyl; and $R_3$ and $R_4$ are each selected from the group consisting of hydrogen, halogen, lower alkyl, nitro, amino, trifluoromethyl, and lower acylamino; at least one of $R_3$ and $R_4$ being a nitrogen containing group, or a pharmaceutically acceptable salt thereof.

In another aspect of the present invention, the method includes administering to an adult patient from about 0.5 mg to about 1.5 mg per day of a benzodiazepine, such as the benzodiazepine having the formula:

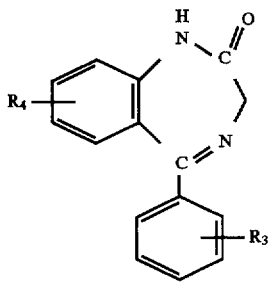

wherein $R_3$ is halogen and $R_4$ is selected from the group consisting of halogen, nitro, and trifluoromethyl or a pharmaceutically acceptable salt thereof.

In a further aspect of the present invention, the method includes administering to a patient selected from the group consisting of an infant and a child from about 0.01 mg/kg to about 0.05 mg/kg of the patient's body weight per day of a benzodiazepine, such as the benzodiazepine having the formula:

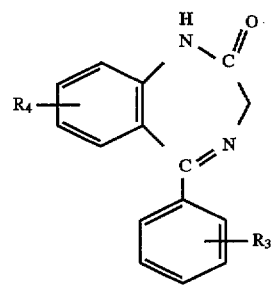

wherein $R_3$ is halogen and $R_4$ is selected from the group consisting of halogen, nitro, and trifluoromethyl or a pharmaceutically acceptable salt thereof.

Employing the methods of the present invention, neurocardiogenic syncope in a patient can be treated.

DETAILED DESCRIPTION OF THE INVENTION

The present invention relates to methods for treating neurocardiogenic syncope.

In one aspect of the present invention, the method includes administering to a patient a benzodiazepine, such as the benzodiazepine having the formula (Formula I):

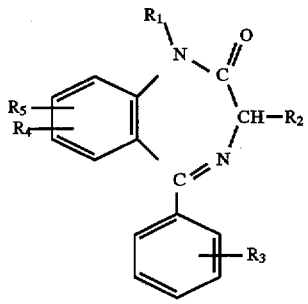

in an effective amount. These compounds are benzodiazepines, which are a class of heterocyclic six-membered ring compounds transformed into hetero-ring compounds with a seven-membered ring.

$R_1$, $R_2$, and $R_5$ are each selected from the group consisting of hydrogen and lower alkyl. Lower alkyls include C1 to C6 alkyls, including linear, branched, and cyclic C1 to C6 alkyls, such as methyl, ethyl, n-propyl, iso-propyl, n-butyl, 1-methylpropyl, 2-methylpropyl, tertbutyl, pentyl, 1-methylbutyl, 2-methylbutyl, 3-methylbutyl 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1-ethyl-1-methylpropyl, and 1-ethyl-2-methylpropyl. When $R_1$, $R_2$ or $R_5$ are a C1 to C6 alkyl, preferably contain from 1 to 4 carbon atoms.

$R_3$ and $R_4$ are each selected from the group consisting of hydrogen, halogen, lower alkyl, nitro, amino, trifluoromethyl, and lower acylamino, with at least one of $R_3$ and $R_4$ being a nitrogen containing group. Halogen includes all four halogens, i.e., chlorine, bromine, iodine, and fluorine. The lower alkyls are as described above. The lower acylamino groups represented by $R_3$ or $R_4$ are those in which the acyl radicals are derived from lower fatty (alkanoic) acids, forming groups such as acetylamino, propionylamino and the like.

Particularly preferred compounds for use in the practice of the present invention are those where $R_1$, $R_2$ and $R_5$ are each hydrogen, $R_4$ is nitro, and $R_3$ is halogen such as chlorine, or those where $R_1$, $R_2$ and $R_5$ are each hydrogen, $R_4$ is halogen, nitro, or trifluoromethyl, and $R_3$ is halogen such as fluorine or chlorine. Most preferably, $R_1$, $R_2$ and $R_5$ are each hydrogen, $R_4$ is nitro, and $R_3$ is chlorine forming the compound known as clonazepam:
5-(2-chlorophenyl)-1,3-dihydro-7-nitro-2H-1,4-benzodiazepin-2-one.

In another aspect of the present invention, the method includes administering to an adult patient from about 0.5 mg to about 1.5 mg per day of a benzodiazepine, such as the benzodiazepine having the formula (Formula II):

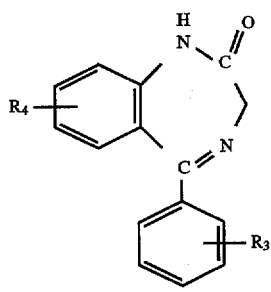

wherein $R_3$ is halogen and $R_4$ is selected from the group consisting of halogen, nitro, and trifluoromethyl or a pharmaceutically acceptable salt thereof. Preferably, $R_3$ is chlorine and $R_4$ is nitro, forming the compound known as clonazepam. The compound is preferably administered in an amount from about 0.5 mg to about 1.0 mg per day.

In a further aspect of the present invention, the method includes administering to a patient selected from the group consisting of an infant and a child from about 0.01 mg/kg to about 0.05 mg/kg of the patient's body weight per day of a benzodiazepine, such as the benzodiazepine having the formula (Formula II):

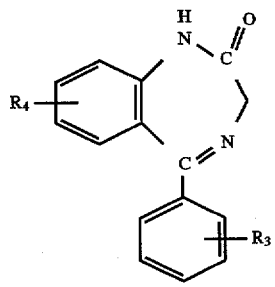

wherein $R_3$ is halogen and $R_4$ is selected from the group consisting of halogen, nitro, and trifluoromethyl or a pharmaceutically acceptable salt thereof. Preferably, $R_3$ is chlorine and $R_4$ is nitro, forming the compound known as clonazepam. The compound is preferably administered in an amount from about 0.01 mg/kg to about 0.03 mg/kg of the patient's body weight per day.

The following is a list of benzodiazepines which can be administered according to the subject invention. The list is merely illustrative and is not intended to be comprehensive:

alpidem
alprazolam
7-aminoclonazepam
7-aminoflunitrazepam
7-aminonitrazepam
bretazenil
bromazepam
chlordiazepoxide
clonazepam
demoxepam
desalkylflurazepam
desalkyl-3-hydroxy-flurazepam
desmethylchlordiazepoxide
diazepam
estazolam
fludiazepam
flunitrazepam
flurazepam
halazepam
4-hydroxyalprazolam
alpha-hydroxyalprazolam
hydroxyethylflurazepam
3-hydroxyprazepam
4-hydroxytriazolam
alpha-hydroxytriazolam
lorazepam
medazepam
midazolam
nitrazepam
norflunitrazepam
oxazepam
prazepam
quazepam
temazepam
triazolam
zolpidem The above described compounds can exist in stereochemically isomeric forms, that is, optical isomers and geometric isomers. Compounds suitable for administration in accordance with this invention include pure optical and geometric isomers or mixtures of these optical and geometric isomers. If desired, the isolation or the production of a particular stereochemical form can be accomplished by application of the general principles known in the prior art.

The method of the present invention may also be practiced using acid-addition salts, preferably pharmaceutically acceptable acid-addition salts, of the compounds of Formula I or II, either in addition to or in place of the compounds of Formula I or II. The acid-addition salt forms of these compounds are structurally the same as the compounds of Formula I or II, except that the cation (generally the proton) of the acid used in their preparation is bonded to the nitrogen, imparting a positive charge thereto, and that the anion of the acid used is present to balance the charge.

These acid-addition salts are prepared from any organic acid; inorganic acid, including organic acids having an inorganic group therein; organo-metallic acid, as exemplified by organic mono- and poly-carboxylic acids, such as those found, for example, in *Beilstein's Organische Chemie*, 4th ed., Volumes III, IV, IX, X, XIV, XVII, XIX, XXI, XXII, and XXV, which are hereby incorporated by reference; organic mono- or poly-sulfonic acids or sulfinic acids, such as those found, for example, in *Beilstein's Organische Chemie*, 4th ed., Volumes VI, XI, XVI, and XXII, which are hereby incorporated by reference; organic phosphonic or phosphinic acids, such as those found, for example, in *Beilstein's Organische Chemie*, 4th ed., Volume XVI, which is hereby incorporated by reference; organic heterocyclic carboxylic, sulfonic, or sulfinic acids, such as those found, for example, in *Beilstein's Organische Chemie*, 4th ed., Volumes XVIII, XXII, and XXV, which are hereby incorporated by reference; acidic ion-exchange resins; or inorganic acids of any acid forming element or combination of elements such as those described in Mellor, *Comprehensive Treatise on Inorganic and Theoretical Chemistry*, Volumes I–XVI, New York: Longman's, Green and Co., which are hereby incorporated by reference. In addition, other salt-forming compounds which are acidic in their chemical properties but which are not generally considered as acids in the same sense as carboxylic or sulfonic acids can be used to prepare the acid-addition salt forms of the compounds useful in practicing this invention. Thus, there are also included acidic phenolic compounds, such as those found, for example, in Volume VI of *Beilstein's Organische Chemie*, 4th ed., which is hereby incorporated by reference, and acidic compounds having "activated" or acidic hydrogen atoms, such as those found, for example, in Cox et al.,*Medicinal Chemistry*, Vol. IV, New York: John Wiley and Sons, Inc. (1959), which is hereby incorporated by reference.

Representative acids for the formation of the acid-addition salts include formic acid, acetic acid, isobutyric acid, alpha-mercaptopropionic acid, trifluoroacetic acid, maleic acid, fumaric acid, succinic acid, succinamic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, and the like. The acid-addition salts with lactic acid and with ethanesulfonic acid, for example, are water-soluble and are especially suitable forms for practicing the present invention.

The acid-addition salts are prepared in conventional fashion, for instance, by direct mixing of the acid and the free base of the compounds having the structure of Formula I or II or their isoelectric forms. When this is not appropriate, acid-addition salt preparation can be effected by dissolving either or both the acid and the free base or isoelectric form separately in water or in an organic solvent and mixing the two solutions or by dissolving both the acid and the free base or isoelectric form together in a solvent. The resulting acid-addition salt is isolated by filtration, if it is insoluble in the reaction medium, or by evaporation of the reaction medium to leave the acid-addition salt as a residue. The acid moieties or anions in the salt forms of the compounds of Formula I or II are not critical and, therefore, can be any acid anion or acid-like substance capable of salt formation with the free base or isoelectric forms of these compounds.

The method of the present invention can be used to treat neurocardiogenic syncope in a patient.

As used herein, neurocardiogenic syncope refers to the clinical syndromes of syncope that result from inappropriate, and often excessive, autonomic reflex activity, and manifest as abnormalities in the control of vascular tone and heart rate. These include carotid sinus syndrome, vasovagal syncope, and the syndromes of cough, deglutition, and micturition syncope. Syncope refers to the sudden transient loss of consciousness (fainting) associated with the inability to maintain postural tone. Pre-syncope refers to premonitory signs and symptoms of imminent syncope.

Patient, as used herein, is generally meant to be a human. An infant or child patient generally refers to a patient up to 10 years of age or 30 kg of body weight.

Treatment, in accordance with the present invention, includes administering to the patient an effective amount of a compound according to Formula I or II or a pharmaceutically acceptable salt thereof.

It will be appreciated that the actual preferred effective amount of compound will vary according to the particular compound, the particular composition formulated, and the mode of administration. Many factors that modify the compound's activity will be taken into account by those skilled in the art; e.g., body weight, sex, diet, time of administration, route of administration, rate of excretion, condition of the patient, drug combinations, and reaction sensitivities and severities. Administration can be carried out continuously or periodically within the maximum tolerated dose.

Preferably, the compound is administered in an amount from about 0.5 mg to about 1.5 mg per day, more preferably, in an amount from about 0.5 mg to about 1.0 mg per day. For an infant or child patient, the compound is preferably administered in an amount from about 0.01 mg/kg to about 0.05 mg/kg of the patient's body weight per day, more preferably, in an amount from about 0.01 mg/kg to about 0.03 mg/kg of the patient's body weight per day. The optimal daily dose for a particular patient can be determined by challenging the patient during a head up tilt test. The optimal daily dose of compound is the minimal dose at which the patient does not experience the symptoms of syncope during the head up tilt test challenge.

The amount can be administered in a single daily dose or in multiple doses or even continuously. Continuous administration can be carried out in the inpatient setting by, for example, intravenous drip, or in an outpatient setting by providing the compound in a slow-release formulation, such as in a suspension or in microcapsules.

Optimal administration amounts and rates for a given patient under a given set of conditions can be ascertained by those skilled in the art using conventional dosage administration tests in view of the above guidelines.

The compound can be administered by any of the conventional modes of drug administration, including oral or parenteral administration. Examples of parenteral administration are intraventricular, intracerebral, intramuscular, intravenous, intraperitoneal, rectal, and subcutaneous administration.

The compounds of the present invention may be administered alone or in combination with suitable pharmaceutical carriers or diluents. The diluent or carrier ingredients should be selected so that they do not diminish the therapeutic effects of the compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, *Encyclopedia of Chemical Technology*, 3rd edition, volume 15, New York:John Wiley and Sons, pp. 470–493 (1981), which is hereby incorporated by reference.

The benzodiazepine compounds employed in the practice of the present invention can be prepared by any suitable method. One method is described in U.S. Pat. No. 3,203,990 to Keller et al., which is hereby incorporated by reference. Briefly, these compounds are derived from substituted 2-aminobenzophenones. Several synthetic routes can be employed.

According to one method, a substituted 2-aminobenzophenone, such as 5-nitro-2-aminobenzophenone, 5-nitro-2-methylaminobenzophenone, and the like is reacted with an a-amino acid or an ester thereof conforming to the formula (Formula III):

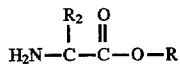

wherein $R_2$ is selected from the group consisting of lower alkyl and hydrogen and R is selected from the group consisting of a lower alkyl and hydrogen.

For example, glycine and lower alkyl glycine esters can be used. Ring closure occurs and a benzodiazepine conforming to Formula I above is obtained wherein $R_2$ is hydrogen and $R_1$, $R_3$, $R_4$ and $R_5$ correspond to the substituents on the 2-aminobenzophenone used as starting material. The use of a longer chain α-amino acid answering to Formula III above wherein $R_2$ is lower alkyl, e.g., alanine, results in a compound of Formula I wherein $R_2$ is a lower alkyl group, i.e., a benzodiazepine containing a lower alkyl substituent in the 3-position.

The reaction of the 2-aminobenzophenone and α-amino acid is preferably effected in a solvent such as pyridine, dimethylformamide or the like. It is also preferable to utilize one of the materials present in the form of a salt of a strong organic or inorganic acid, e.g., glycine hydrochloride, glycine ethyl ester hydrochloride, alanine hydrochloride, pyridine hydrochloride, or the like.

According to an alternate method, the substituted 2-aminobenzophenone can be haloacylated, such as with bromoacetyl bromide, α-bromopropionyl bromide, chloroacetyl chloride, or the like, to yield a 2-(α-halo-lower alkanoylamino)-benzophenone of the formula (Formula IV):

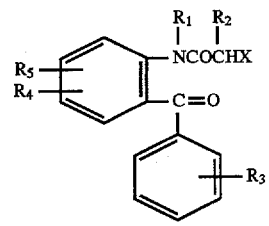

wherein X is halogen; $R_1$ and $R_2$ are each selected from the group consisting of hydrogen and lower alkyl; $R_3$, $R_4$ and $R_5$ are each selected from the group consisting of hydrogen, halogen, lower alkyl, nitro, amino and lower acylamino; at least one of $R_3$, $R_4$ and $R_5$ being a nitrogen containing group.

The resultant haloacylated-2-aminobenzophenone can then be treated with ammonia. This treatment with ammonia effects ring closure to obtain a benzodiazepine conforming to Formula I above. It is most convenient from a viewpoint of operating economically and ease of handling to use alcoholic ammonia; however, other ammonia solutions can be used as is readily apparent to those skilled in the art.

Benzodiazepines conforming to Formula I above can also be prepared by cyclizing a 2-(α-amino-lower alkanoylamino)-benzophenone.

The preferred compound for use in the method of the subject invention, clonazepam, can be prepared as specifically described in U.S. Pat. No. 3,123,529 to Kariss and Newmark, which is hereby incorporated by reference.

A stirred solution of 75 g. of 2-amino-2'- nitrobenzophenone in 700 ml. of hot concentrated hydrochloric acid is cooled to 0° and a solution of 21.5 g. of sodium nitrite in 50 ml. of water is added in the course of 3 hours. The temperature of the suspension is kept at 2–7° during the addition. The resulting clear solution is poured into a stirred solution of 37 g. of cuprous chloride in 350 ml. of hydrochloric acid 1:1. The solid which has formed after a few minutes is filtered off, washed with water and recrystallized from ethanol. Crystals of 2-chloro-2'-nitrobenzophenone melting at 76–79° are obtained.

A solution of 20 g. of 2-chloro-2'-nitrobenzophenone in 450 ml. of ethanol is hydrogenated at normal pressure and room temperature with Raney nickel. After uptake of about 6 liters of hydrogen, the catalyst is filtered off, and the alcohol is then removed in vacuo. The residue is distilled in a bulb tube at 0.4 mm. and a bath temperature of 150–165° giving a yellow oil. The oil is dissolved in alcohol, and on addition of water, needles of 2-amino-2'-chlorobenzophenone melting at 58–60° are obtained.

To a solution of 42 g. of 2-amino-2'-chlorobenzophenone in 500 ml. of benzene, 19 ml. of bromoacetyl bromide is added dropwise. After refluxing for 2 hours, the solution is cooled, washed with 2 N sodium hydroxide and evaporated. The residue is recrystallized from methanol giving crystals of 2-bromo-2'(2-chlorobenzoyl) cetanilide melting at 119–121°.

To a solution of 14.5 g. of(2-bromo-2'-(2-chlorobenzoyl) acetanilide in 100 ml. of tetrahydrofuran, an excess of liquid ammonia (about 150 ml.) is added. The ammonia is kept refluxing with a Dry-Ice condenser for 3 hours after which time the ammonia is allowed to evaporate and the solution is poured into water. Crystals of 2-amino-2'-(2-chlorobenzoyl) acetanilide are collected, which after recrystallization from ethanol melt at 162–164°.

A solution of 3 g. of 2-amino-2'-(2-chlorobenzoyl) acetanilide in 50 ml. of pyridine is refluxed for 24 hours after which time the pyridine is removed in vacuo. The residue is recrystallized from methanol and a mixture of dichloromethane and ether giving crystals of 5-(2-chlorophenyl)-3H-1,4-benzodiazepin-2(1H)-one melting at 212-213°.

To a solution of 13.5 g. of 5-(2-chlorophenyl)-3H-1,4-benzodiazepin-2(1H)-one in 60 ml. of concentrated sulfuric acid, a solution of 5.5 g. of potassium nitrate in 20 ml. concentrated sulfuric acid is added dropwise. The solution is then heated in a bath at 45–50° for 2½ hours, cooled and poured on ice. After neutralizing with ammonia, the formed precipitate is filtered off and boiled with ethanol. A small amount of white insoluble material is then filtered off. The alcoholic solution on concentration yields crystals of 7-nitro-5-(2-chlorophenyl)-3H-1,4-benzodiazepin-2(1H)-one (clonazepam) which, after recrystallization from dichloromethane, melt at 238–240°.

Further descriptions of the preparation of benzodiazepines such as clonazepam are provided in Sternbach et al. 1963 and U.S. Pat. Nos. 3,116,203 to Kariss and Newmark, 3,121,114 to Keller et al., 3,335,181 to Focella and Rachlin, 4,772,599 to Watjen, 5,302,715 to Buechler and Noar, and 5,317,018 to Walser et al., the contents of each of which are incorporated by reference.

The present invention is further illustrated by the following examples.

EXAMPLES

Example 1 —Subjects

Twenty-two (22) human patients with recurrent severely symptomatic refractory neurocardiogenic syncope (NCS)/pre-syncope were selected. Diagnosis of NCS was established by history, physical examination, exclusion of other etiologies for syncope, and positive head up tilt study with reproduction of symptoms.

Patient characteristics were as follows:

| Age (years) | 52.5 ± 22.4 | |
|---|---|---|
| Males | 12 | (54.5%) |
| Organic Heart Disease | | |
| a. Hypertension | 9 | (40.9%) |
| b. CAD | 8 | (36.3%) |
| c. Cardiomyapathy | 3 | (13.6%) |
| d. Impaired LVSF | 4 | (18.1%) |
| e. MVP | 2 | (9.0%) |
| f. SSS | 6 | (27.2%) |
| Associated sleep disorders | 8 | (36.3%) |
| Number of drugs failed | 2.1 ± 1.0 | |
| Chronic fatigue syndrome | 3 | (13.6%) |
| Concomitant Beta blockers | 9 | (40.9%) |

LVSF=Left ventricular systolic function.
MVP=Mitral valve prolapse.
SSS=Sick sinus syndrome.

Prior to clonazepam initiation, subject medication and therapeutic modalities included (unless contraindicated) beta blockers, high salt diet, Florinef, elastic stockings, Disopyramide, and/or pacemaker. Response to therapy was considered ineffective if symptoms recurred, intolerance to therapy occurred, and/or the head up tilt test (HUT) reproduced significant clinical symptoms in less than 30 minutes at 70° tilt. All patients had normal liver function studies and electroencephalogram as well as abnormal HUT.

Example 2 - Treatment of subjects with clonazepam

The 22 patients with recurrent severely symptomatic refractory NCS/pre-syncope were given clonazepam at 0.5–1.0 mg dose (in the form of commercially available KLONOPIN® tablets marketed by Roche Laboratories, Nutley, N.J.). Nine of the 22 patients continued beta blocker regimens (Lopressor 25–50 mg bid or its equivalent) because of hypertension, arrhythmia, or coronary artery disease.

Clonazepam treatment began at 0.5 mg dose. Early phase follow up (FU) at 1–2 weeks included a clinic visit with clonazepam dose titration at 0.25–0.5 mg increments according to symptom recurrence and significantly positive HUT. Late FU at 2–4 months included clinic visit and HUT even if asymptomatic to ensure absence of tachyphylaxis. If clonazepam failed at any level, other drugs (mainly beta blocker at a small dose) and/or other intervention were added at the discretion of the treating cardiologist. Clonazepam was discontinued if significant side effects developed or if the patient withdrew from the study.

Example 3 - Results of treatment

Twenty-two (22) patients with a follow-up of 5.9 ±5.5 months at a dose of 0.73 ±0.23 mg were followed. Range of follow-up was 0.5–24 months. At early follow up, symptom control occurred in 21 patients with symptoms reduced in one patient. Three of the 21 patients did not have the early phase HUT. In two of the 21 patients, the drug was discontinued within two weeks of therapy because of side effects (psychosis in one patient and behavioral changes in one patient). The one of the 22 patients had symptoms controlled. Follow up HUT was positive. Beta blocker was added to the therapy which lead to symptom control. The patient always continued to have positive HUT. At 5 months follow up, the patient developed transient ischemic attacks and the neurologist discontinued beta blockers and clonazepam. The patient was lost for follow since then. Sixteen of the 21 patients had early phase HUT. Fifteen of the 16 patients had negative HUT following treatment. In one of the 15 patients the medication was discontinued because of side effects (dry mouth and weakness). The other one of the 16 patients had positive HUT and beta blocker was added and had complete control over symptoms. Chronic phase follow up HUT is pending for this patient. Eleven of the 14 patients remaining on treatment with negative HUT after treatment were followed for greater than 2–4 months. They all were asymptomatic. HUT at 2–4 months follow up was negative in these 11 patients. Subsequently two of the 14 patients discontinued the clonazepam, one due to side effects (headache) and the other withdrew from the study (no side effects). Twelve of the 14 patients continued without symptoms and tolerated the medication well.

To summarize these results, of the 14 patients (8 males, 6 females, age 18–84 years) who were followed for 6 weeks to 10 months, all had initial improvement of symptoms of NCS following initial treatment at 0.5 mg clonazepam. One patient withdrew from the study. At early follow up phase, 12 of the 14 patients had negative HUT. Four of 8 required increasing the dose of clonazepam to 1.0 mg because of recurrence of mild symptoms. At 0.5–1.0 mg, seven of 8 patients had no significant neurocardiogenic symptoms. Three of eight patients failed HUT however. The six remaining patients had not reached the four month follow up.

Side effects included early sedation in 20 patients (90.9%) which persisted in two patients (9.1%); dry mouth in one patient (4.5%), headache in two patients (9.1%), psychosis in one patient (4.5%), imbalance in one patient (4.5%), behavioral changes in two patients (9.1%), which subsided with decrease in dose in one patient, and nausea in one patient (4.5%). Side effects required discontinuation of treatment in four patients (18.1%).

Clonazepam thus is a centrally acting medication at a small dose (0.5 to 1.5 mg) and is well tolerated, and is clinically effective in the treatment of symptomatic and refractory neurocardiogenic syncope. No significant development of tolerance to clonazepam on chronic follow up occurred. The very small daily doses of clonazepam necessary for effective treatment should provide a safer side effect profile than the side effect profiles seen with traditionally prescribed medicines for chronic neurocardiogenic syncope. Such traditional treatments include beta blockers, the hormone florinef, and anti-arrhythmic drugs. Side effects from beta blockers may include weakness, slowed heart rate, impotence, low blood pressure, and depression. Side effects with florinef include high blood pressure, headache, visual problems, swelling of the extremities and potassium deficiencies. Patients on anti-arrhythmic drugs may suffer from severe dry mouth and abnormal heart rhythms and, in some cases, such drugs can lead to congestive heart failure and/or sudden death. In contrast, the most common side effects of clonazepam include drug dependence, behavior change, sleepiness and headache; effects that are seen infrequently when the drug is prescribed in the small doses used to treat neurocardiogenic syncope.

Although the invention has been described in detail for the purpose of illustration, it is understood that such detail is solely for that purpose, and variations can be made therein by those skilled in the art without departing from the spirit and scope of the invention which is defined by the following claims.

LIST OF REFERENCES CITED

Abi-Samra et al., Pacing Clin Electrophysiol 11(8) :1202–1214 (1988).
Chen et al., Am J Cardiol 69:755–760 (1992).
Fitzpatrick et al., Lancet 1(8639):658–660 (1989).
Fitzpatrick et al., J Am Coll Cardiol 17 (1): 125–130 (1991a).
Fitzpatrick et al., Pacing Clin Electrophysiol 13(5):619–624 (1991b).
Fouad et al., Pacing Clin Electrophysiol 16(3 Pt 1):394–400 (1993).
Grubb et al., Am J Med 90(1):6–10 (1991).
Grubb et al., Pediatr Neurol 8 (6) :423–427 (1992a).
Grubb et al., Otolaryngol Head Neck Surg 107(4):570–576 (1992b).
Grubb et al., Heart Lung 22(6):502–508 (1993).
Kapoor, JAMA 268 (18) :2553–2560 (1992).
Kenny et al., Lancet 1(8494):1352–1355 (1986).
Kosinski et al., Pacing Clin Electrophysiol 18(4 Pt 1):716–724 (1995).
Lipsitz et al., J Chronic Dis 39(8):619–630 (1986).
Lipton and Forstater, J Emerg Med 11(6):723–727 (1993).
Milstein et al., Am J Cardiol 65(20):1339–1344 (1990).
Natale et al., Pacing Clin Electrophysiol 18(4 Pt 1):655–662 (1995).
Raviele et al., Am J Cardiol 65:1322–1327 (1990).
Sra et al., Cardiol Clin 11(1):183–191 (1993a).
Sra et al., N Engl J Med 328(15):1085–1090 (1993b).
Sternbach et al., J Med Chem 6:261–265 (1963).
Sutton and Petersen, J Cardiovasc Electrophysiol 6 (7):569–576 (1995).

What is claimed is:

1. A method for treating neurocardiogenic syncope in a patient, said method comprising:

administering to an adult from about 0.5 milligrams to about 1.5 kilograms per day, or to a child from about 0.01 milligrams per kilogram to about 0.05 milligrams per kilogram of the child's body weight per day, of a compound having the formula:

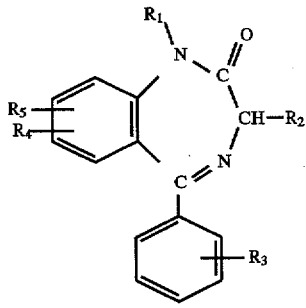

wherein $R_1$, $R_2$ and $R_5$ are each selected from the group consisting of hydrogen and lower alkyl; and $R_3$ and $R_4$ are each selected from the group consisting of hydrogen, halogen, lower alkyl, nitro, amino, trifluoromethyl, and lower acylamino; at least one of $R_3$ and $R_4$ being a nitrogen containing group, or a pharmaceutically acceptable salt thereof.

2. The method of claim 1 wherein $R_1$, $R_2$ and $R_5$ are each hydrogen, $R_4$ is nitro, and $R_3$ is a halogen.

3. The method of claim 2 wherein $R_3$ is chlorine.

4. The method of claim 3 wherein the compound is clonazepam.

5. The method of claim 1 wherein $R_1$, $R_2$ and $R_5$ are each hydrogen, $R_4$ is selected from the group consisting of halogen, nitro, and trifluoromethyl, and $R_3$ is halogen.

6. The method of claim 5 wherein $R_3$ is selected from the group consisting of fluorine and chlorine.

7. The method of claim 1 wherein the compound is contained in a slow-release microcapsule or suspension formulation.

8. The method of claim 1 wherein the compound is administered orally.

9. The method of claim 8 wherein the compound is in a tablet, capsule, granule, dispersible powder, suspension, syrup, or elixir form.

10. The method of claim 9 wherein the compound is in a tablet or capsule form and is admixed with inert diluent, granulating agent, disintegrating agent, a lubricating agent, or combinations thereof.

11. The method of claim 9 wherein the compound is in a suspension and is admixed with inert diluent, excipients, wetting agents, preservatives, or combinations thereof.

12. The method of claim 1 wherein the patient is an adult and the compound is administered in an amount from about 0.5 mg to about 1.0 mg per day.

13. The method of claim 1 wherein the patient is a child, and the compound is administered in an amount from about 0.01 mg/kg to about 0.03 mg/kg of the patient's body weight per day.

14. A method for treating neurocardiogenic syncope in an adult patient, said method comprising:

administering to the adult patient from about 0.5 mg to about 1.5 mg per day of a compound having the formula:

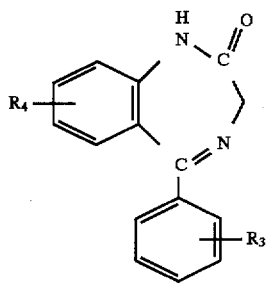

wherein $R_3$ is halogen and $R_4$ is selected from the group consisting of halogen, nitro, and trifluoromethyl or a pharmaceutically acceptable salt thereof.

15. The method of claim 16 wherein $R_3$ is chlorine and $R_4$ is nitro.

16. The method of claim 17 wherein the compound is clonazepam.

17. The method of claim 16 wherein the compound is administered in an amount from about 0.5 mg to about 1.0 mg per day.

18. A method for treating neurocardiogenic syncope in a patient wherein the patient is a child, said method comprising:

administering to the patient from about 0.01 mg/kg to about 0.05 mg/kg of the patient's body weight per day of a compound having the formula:

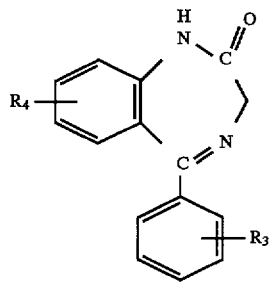

wherein $R_3$ is halogen and $R_4$ is selected from the group consisting of halogen, nitro, and trifluoromethyl or a pharmaceutically acceptable salt thereof.

19. The method of claim 18 wherein $R_3$ is chlorine and $R_4$ is nitro.

20. The method of claim 19 wherein the compound is clonazepam.

21. The method of claim 18 wherein the compound is administered in an amount from about 0.01 mg/kg to about 0.03 mg/kg of the patient's body weight per day.

* * * * *